United States Patent [19]
Nelson et al.

[11] Patent Number: 5,302,747
[45] Date of Patent: Apr. 12, 1994

[54] PROCESS FOR THE MANUFACTURE OF ESTERS

[75] Inventors: Philip E. Nelson, West Lafayette, Ind.; Athula Ekanayake, Cincinnati, Ohio

[73] Assignee: Purdue Research Foundation, West Lafayette, Ind.

[21] Appl. No.: 934,770

[22] Filed: Aug. 24, 1992

[51] Int. Cl.⁵ .............................................. C07C 67/02
[52] U.S. Cl. .................................................. 560/265
[58] Field of Search ......................................... 560/265

[56] References Cited

U.S. PATENT DOCUMENTS

| | | | |
|---|---|---|---|
| 1,454,462 | 5/1923 | Backhaus | 560/265 |
| 2,015,870 | 10/1935 | Ricard et al. | 260/488 |
| 3,131,212 | 4/1964 | Biller | 260/468 |
| 3,845,121 | 10/1974 | Eubanks et al. | 562/519 |
| 5,144,068 | 9/1992 | Smith et al. | 562/519 |

*Primary Examiner*—Arthur C. Prescott
*Attorney, Agent, or Firm*—Woodard, Emhardt, Naughton, Moriarty & McNett

[57] ABSTRACT

A method and apparatus for producing esters without the aid of a conventional acid catalyst. A mixture of a monohydric aliphatic alcohol and a lower carboxylic acid is provided in a reaction vessel equipped with a fractionating column connected to a condenser and a collecting vessel. Heating means and a device for passing small bubbles of gas through the reactants are included. The alcohol/carboxylic acid mixture is maintained at a temperature of at least about the boiling point of the alcohol, but below about the boiling point of the carboxylic acid, and a gas inert to the esterification reaction is bubbled through the mixture to remove the esterification product therein formed. The removed vapors are collected and condensed, and the esterification product is recovered in high conversion and purity.

22 Claims, 1 Drawing Sheet

PROCESS FOR THE MANUFACTURE OF ESTERS

BACKGROUND OF THE INVENTION

This invention relates generally to the manufacture of esters, and more particularly to a process for the efficient, economic manufacture of such esters, and especially ethyl acetate, without the need of a conventional catalyst.

The production of many esters is accomplished by the reaction of an alcohol with a carboxylic acid. For example, ethyl acetate has long been produced commercially according to the following reaction:

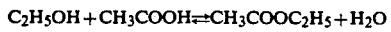

$$C_2H_5OH + CH_3COOH \rightleftharpoons CH_3COOC_2H_5 + H_2O$$

This reaction is known to proceed slowly however, so that without the use of a catalyst to promote the forward reaction, equilibrium is established after several weeks at room temperature. Because this rate of reaction is not satisfactory for commercial applications a strong acid catalyst is often used to drive these reactions. For example, both concentrated sulfuric acid and hydrogen chloride gas have been used and are known to be particularly effective esterification catalysts in such reactions. These catalysts drive the reactions through to equilibrium more rapidly, i.e., within a matter of hours.

The use of such acids to catalyze esterification reactions may not be favored however. Acid catalysts also promote numerous side reactions to varying degrees resulting in small amounts of contaminants, some of which have very low sensory thresholds. As a result, synthetic ethyl acetate esters made from petroleum-based alcohols and carboxylic acids may have objectional sensory profiles.

In addition, acid catalysts are not acceptable for use in a particular and growing segment of the food industry which requires "naturally-made" esters for certain products. For example, "naturally-made" ethyl acetate is commercially useful for "natural decaffeination" processes for coffee. Other potential uses of natural esters include the preparation of certain pharmaceutical products and as direct food additives in natural flavor extracts.

Presently, such "naturally-made" esters are largely produced as by-products of certain fermentation processes. Unfortunately, the cost of manufacturing such "naturally-made" esters can be prohibitively high. For example, at current market prices, the cost of "naturally-made" ethyl acetate is approximately $10.00/lb. In addition, the purities of the product esters from such processes are unsatisfactory in many cases. For example, the purity of ethyl acetate commercially produced as a fermentation by-product rarely exceeds 90% to 92%. A variety of undesirable contaminants are also typically found in the resulting acetates when such processes are employed.

Accordingly, there is a need for a method of efficiently and economically producing esters without the aid of conventional acid catalysts. The present invention addresses that need.

SUMMARY OF THE INVENTION

Briefly describing the present invention, there is provided a method and related apparatus for producing esters without the use of a conventional acid catalyst. In one embodiment, a monohydric aliphatic alcohol having from one to four carbon atoms and a lower carboxylic acid having from one to about four carbon atoms are mixed together in a reaction vessel equipped with a fractionating column connected to a condenser and a collecting vessel. A device for dispersing small bubbles of gas such as air up through this reaction mixture is also included. The alcohol/carboxylic acid mixture is brought to a temperature of about the boiling point of the alcohol or slightly higher, but preferably lower than the boiling point of the carboxylic acid reactant, and small bubbles of the gas are released up through the heated mixture and the vapors are collected and condensed. Following distillation and purification of the condensate, a commercial quality and quantity "naturally-made" ester has been shown to be economically produced.

One object of the present invention is thus to provide a method of making esters without the use of a conventional catalyst.

Another object of the present invention is to provide an environmentally friendly method of making "naturally-made" esters, so that the only products of the reaction are the desired ester, pure water and weak solutions of the reactants which can be recovered for reuse.

Another object of the present invention is to provide a method of producing "naturally-made" esters which are relatively pure and contain no harmful or sensorially objectionable contaminants.

Related objects and advantages of the present invention will be apparent from the following description.

DESCRIPTION OF THE PREFERRED EMBODIMENT

Figure 1:
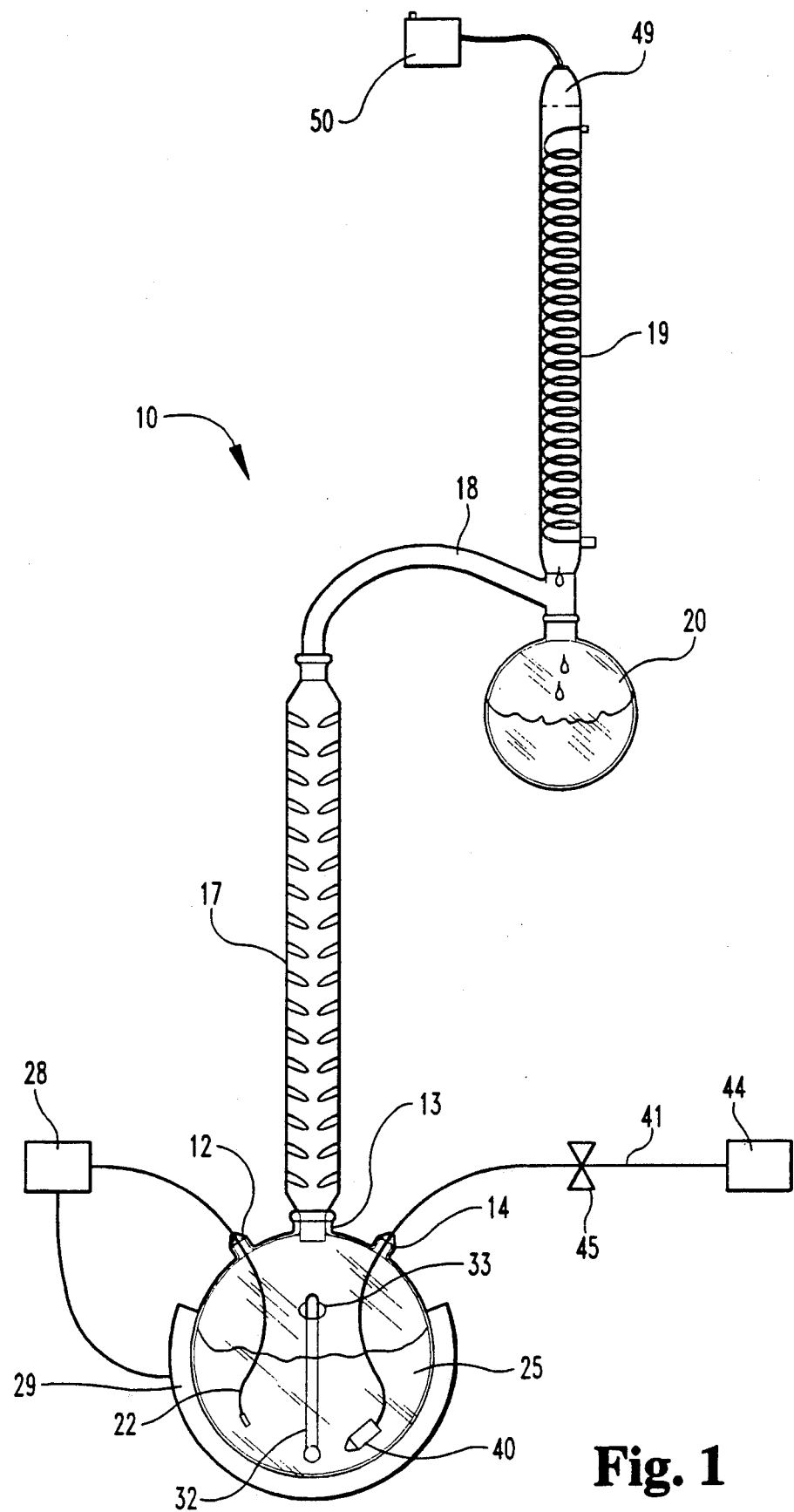
FIG. 1 illustrates the apparatus of the present invention according to one preferred embodiment.

For the purposes of promoting an understanding of the principles of the invention, reference will now be made to the preferred embodiments illustrated in the examples and specific language will be used to describe the same. It will nevertheless be understood that no limitation of the scope of the invention is thereby intended, such alterations and further modifications in the illustrated process and apparatus, and such further applications of the principles of the invention as illustrated therein, being contemplated as would normally occur to one skilled in the art to which the invention relates.

The present invention relates to a method of, and related apparatus for, promoting the production and recovery of esters by bubbling a gas through a heated alcohol/carboxylic acid reaction mixture. Esters within the scope of this invention are low boiling esters which may be produced by reacting a monohydric aliphatic alcohol having from one to about four carbon atoms with a lower carboxylic acid having between one and about four carbon atoms in the chain. Examples of such low boiling esters include ethyl acetate, ethyl formate, ethyl propionate, ethyl butyrate, methyl formate, methyl acetate, methyl propionate and the like. Examples of their precursor reactants and further discussion of the scope and breadth of applicants' invention follows in the specific examples and paragraphs below.

Concerning one aspect of the invention, one embodiment comprises a method including mixing a monohydric aliphatic alcohol and a lower carboxylic acid as described herein in a reaction pot to thereby begin the ester formation. The reactants are then preferably brought to a temperature, by heating if necessary, which is about at or slightly higher than the boiling point of the alcohol and small gas bubbles inert to the reaction are passed through the reaction mix. The preferred apparatus is arranged such that these gas bubbles can exit the reaction vessel only through a fractionating column attached to a cold water condenser. The effluent vapors are fractionated in the column and the distillate is collected. Although not yet concentrated, this distillate has been found to consist of at least about 20% ester, about 70% alcohol and the remaining about 10% water.

The efficiency of this forward reaction has been shown to be increased by decreasing the size of the gas bubbles passing through the reacting system. For example, in the case of ethyl acetate production, a standard gas bubbler with 1 mm holes produced about 16–18% ethyl acetate in this distillate. A stainless steel filtering device with 10 μm pore size produced about 26–30% ethyl acetate in this distillate when other conditions remained the same. Further evidence of this aspect of applicants' invention is found in the specific examples below.

Once collected, this distillate from the reaction is then preferably subjected to reflux using an efficient fractionating column and the ternary azeotrope for each ester (which is known to be comprised primarily of the ester, with some alcohol and water included) is distilled from it. The bottoms remaining in the pot (which comprise primarily alcohol and some water) are preferably returned to the reaction vessel to increase reactant concentration in later runs.

In experiments to date, the above aspect of the invention has been operated as a batch process. In such a process, it has been preferred to repeat the above-described procedure several times, most preferably three times, until the carboxylic acid concentration in the reaction vessel is too low to promote further reaction. By so doing, a conversion efficiency of about 85% to 90% in terms of acid consumption has been obtained by this procedure, as in the case of ethyl acetate production and in the examples below. This amount compares very favorably with the about 95% yield which has been claimed for batch processes using an acid catalyst such as those described above. Alternatively, the method of the present invention may be operated as a continuous process whereby reactants are continually added to the reaction pot as product is drawn off and recaptured reactant is recycled.

Regarding the level of heating desired, experiments to date have shown that it is preferable for the reaction mix to be at a temperature of about at or slightly (up to about 15° C. from experiments thus far) higher than the boiling point of the alcohol, but lower than that of the carboxylic acid reactant. The vapor pressure of the alcohol in the pot is thus increased while the carboxylic acid remains predominantly in the reaction mix. From testing to date, maintaining this temperature during the gas bubbling has shown to increase ester formation and removal from the reaction mixture for subsequent isolation and recovery. This testing has also shown that starting with a stoichiometric excess of alcohol in the reaction mixture in the case of a batch process (and maintaining some excess in a continuous process) is preferred to more efficiently practice the method of the present invention. In practice, once the alcohol and carboxylic acid reactants have been selected for a particular commercial application, adjustments in this desired temperature and other reaction conditions to maximize efficiency can be made by the operator and are well within the knowledge and experience of those ordinarily skilled in this area. Accordingly, such variations and adjustments are within the scope of applicant's invention as disclosed and claimed herein.

The rate, size and quantity of gas bubbling through the reactants have also been found to affect the efficiency and thus economy of the reaction. In particular, the rate of bubbling is preferably slow enough that the vaporized ester is not exhausted through the condensing column before all or predominantly all of the desired product can be condensed and collected. As mentioned earlier, and as discussed in more detail in the examples to follow, the size of gas bubbles passing through the reactants also affects the rate of ester recovery as smaller bubbles have shown to increase reaction efficiency significantly. Similarly, greater amounts of gas bubbles passing through the reactants also increase ester removal to the atmosphere for its subsequent recovery. Understandably, the economics of a commercial application make it desirable to bubble gas through the reaction mixture at a rate, size and amount to most efficiently promote the production and recovery of the desired ester. Accordingly, a balance must be struck in each commercial application to maximize efficiency and adjustments in these and other reaction conditions will be made by the operator to accomplish this result. Such adjustments are well within the knowledge and experience of those ordinarily skilled in this area, and will depend to a great extent on the efficiency of the condensing column and other characteristics of the apparatus being used in each case. As to the gas itself, air has been preferred to date although other gases inert to the esterification reaction can also be used.

Concerning now another aspect of the present invention, a representative embodiment of a preferred apparatus is shown in FIG. 1. Esterification apparatus 10 includes a reaction pot 11 having three necks 12, 13 and 14. A fractionating column 17 is installed in center neck 13. A connector 18 is attached to the top of the fractionating column, so that condenser 19 and collecting flask 20 may be attached thereto.

A thermocouple 22 is installed in the reaction vessel through neck 12, and is kept immersed in the reactants 25 in the bottom of the reaction vessel. Thermocouple 22 is connected to a controller 28, which regulates the heat provided to reaction pot 11 by heating mantle 29. A thermometer 32 is inserted through the thermometer aperture 33 provided in the pot to monitor the temperature of the reaction.

A stainless steel filtering device 40 is installed in air inlet line 41 and is placed in the bottom of the pot. The filtering device 40 is used to provide small air bubbles when air from the source 44 of compressed air passes through air inlet line 41. The rate and thereby amount of air bubbling is preferably controlled by a needle valve 45 located in the air inlet line. The rate of air bubbling can be monitored by placing an air flow meter (not shown) at the upper end 49 of the condenser. In operation, however, it is preferred to connect a charcoal trap 50 to the upper end 49 of condenser 19, so that the bubbled air is scrubbed before its release to the atmosphere.

Concerning the specific components making up apparatus 10, the individual selection of these components and their assembly and operation in connection with the preferred method described above are well within the knowledge and experience of those persons ordinarily skilled in this area. For example, the reaction pot and connecting pieces may be made of any non-reactive material. Glass and/or stainless steel have been used in experiments to date due in part to their low cost and ready availability. The fractionating column may be of any efficient design. A Vigreux column was used in the examples described herein, but other suitable columns may be obtained commercially or constructed from available parts by persons ordinarily skilled in this field. Preferably, the length of the column along with other factors are selected such that the column acts to efficiently condense the ester vapors before they are exhausted from the column.

Similarly, the air filter/bubbling device may be of any material or design suitable to produce air bubbles in the reaction pot without, of course, the device itself reacting with the reactants. In testing to date, it has been preferred to provide an apparatus which will produce the smallest air bubbles possible as discussed above. In the described experiments, for example, a stainless steel filter such as is used for high pressure liquid chromatography (HPLC) was installed in the reaction pot to provide the air bubbles. Air bubbles as small as 0.5 $\mu$m have been produced by this apparatus, with the greatest reaction efficiency being obtained when the smallest air bubbles were used.

Reference will now be made to specific examples using the method and apparatus described above. It is to be understood that these examples are provided to more completely describe and explain these preferred embodiments, and that no limitation to the scope and breadth of the invention is thereby intended.

EXAMPLE 1

Two liters of fermentation grade absolute ethanol and two liters of fermentation grade 300 grain vinegar (30% acetic acid) were mixed and placed in the apparatus 10 shown in FIG. 1. A stainless steel 10 $\mu$m filtering device connected by a stainless steel tube to a source of compressed air was used as the bubbling device. As is shown in FIG. 1, the arrangement was such that when air was bubbled in through the filtering device it could exit the flask only through the fractionating column. The rate of air flow through the air inlet line was controlled by the operator using a needle valve located in the line. The reactants were then heated to 85° C., and the temperature was maintained at that point. Upon reaching this temperature, air bubbling was begun at a rate not exceeding 200 ml/min. measured at the end of the condenser. The reaction was allowed to proceed for 36 hours from the time air bubbling was begun. At the end of this initial reaction time, the receiving flask had a product volume of 1540 ml, which upon analysis was found to consist of 32% ethyl acetate, 67% ethanol and 1% water. After withdrawing the contents, the receiving flask was replaced and the reaction continued. The product was diluted with water to 10% and subjected to distillation using an efficient fractionating column. The distillate consisted of approximately 80% ethyl acetate, 10% ethanol and 10% water. The bottoms were tested and shown to consist of approximately 2% ethyl acetate, 80% ethanol and 8% water. The bottoms were added back to the reaction flask, while the distillate rich in ester was kept for further processing.

After another 24 hours (total reaction time of 60 hours), a fraction of 1340 ml was collected in the receiving flask. This was also distilled, and the bottoms were added back to the reacting flask as before.

After a final 24 hours of reaction time (total reaction time 84 hours), another 770 ml was collected and the reaction was stopped. The product was distilled to recover the ethyl acetate-rich fraction and the bottoms were stored for further use as feedstock.

The contents of the reaction flask at the end of the reaction consisted of 2000 ml of liquid made up of 19% ethanol, 0.2% ethyl acetate, 5% acetic acid and 76% water. The pooled ethyl acetate-rich fractions were subjected to purifications steps as are known in the art and a product containing more than 99.5% pure "naturally-made" ethyl acetate was recovered. This equated to a conversion efficiency of 85% to 90% in terms of acetic acid consumption, which compares very favorably with the 95% yield claimed for prior art batch processes of this reaction using one of the acid catalysts previously known for this purpose.

EXAMPLE 2

One liter of 95% ethanol and one liter of 300 grain vinegar (30% acetic acid) were combined in apparatus 10 of FIG. 1. In this experiment, an air bubbler having a hole diameter of approximately one millimeter was immersed in the reactants. Air was bubbled in at 90 ml ($\pm$1 ml) per minute and the reaction was allowed to proceed for between 15 and 20 hours. This time was measured from the point at which the reactants reached 85° C. and the air supply was begun to the point where the air supply was terminated.

The volume of product in the collection flask was measured to be 325 ml, and its ethyl acetate content was determined to be 30.4% (98.83 ml). The contents of the reaction vessel were cooled to room temperature and its volume was determined to be 1620 ml. The ethyl acetate content was determined to be 2.84% (27.2 ml). The rate of reaction was then calculated in moles per liter per hour (m/L/h) of ethyl acetate produced, taking into account the residual ethyl acetate remaining in the reaction vessel. When the 1 mm air bubbler was used this rate of production of ethyl acetate was approximately 0.042 m/L/h. This rate calculation is yet another way to quantify the efficiency of a reaction generally, and another way in this case to demonstrate the increased efficiency of applicants' preferred method over those used in the prior art. This comparison will be more evident in Examples 3–7, which compare the performance of varying bubble size against a prior art control run.

EXAMPLES 3–7

Further experiments in accordance with the foregoing description in Example 2 were performed using air bubblers having hole diameters of 10 $\mu$m, 5 $\mu$m, 2 $\mu$m and 0.5 $\mu$m. A control experiment having no air bubbles passing through the reaction mixture was also performed. For the experiments using air bubbles, air was bubbled once again at a rate of 90 ml ($\pm$1 ml) per minute, and the reaction of each run was allowed to proceed for between 15 and 20 hours. The calculated rate of production of ethyl acetate in each run is shown in the following table.

TABLE 1

| Nominal bubbler hole diam. ($\mu$m) | Rate of production of ethyl acetate (m/L/h) |
|---|---|
| Control (no air bubbled) | 0.037 |

TABLE 1-continued

| Nominal bubbler hole diam. (μm) | Rate of production of ethyl acetate (m/L/h) |
| --- | --- |
| 1000 | 0.042 |
| 10 | 0.046 |
| 5 | 0.048 |
| 2 | 0.051 |
| 0.5 | 0.052 |

It can be seen from this data that the rate of production of ethyl acetate in these tests was dependent, at least in part, upon this nominal bubbler hole diameter and the resultant size of bubbles passing through the reactants. In particular, the smaller the bubbles the greater the rate of production of ethyl acetate. The volume of air bubbled remained constant through these runs.

Although the precise mechanism by which bubbles passing through a heated reaction zone promote the esterification process is not completely understood, it is believed that the bubbling gas assists in removing the ester as it is formed, thereby driving the reaction forward to the right in an attempt to achieve equilibrium. It is further believed that passing smaller air bubbles through the reaction zone better assists in removing ester from the reaction mix due to the effect of increased bubble surface area. Accordingly, both theory and experimental data indicate that the selection of an optimal bubble size may be determined for a particular application by one skilled in the art without undue experimentation.

EXAMPLE 8

Still further examples of the production of various low boiling esters in accordance with the foregoing description were performed using apparatus 10 of FIG. 1 and appropriate alcohol/carboxylic acid mixes under conditions, including temperatures, effective for the individual reactions as known to those ordinarily skilled in this area. To make ethyl formate, ethanol and formic acid were mixed in the apparatus of FIG. 1 and the reactants were heated to approximately 80° C. An air bubbler having a hole diameter of approximately 1.0 μm was immersed in the reactants, Air was bubbled in at 90 ml (±1 ml) per minute, and the reaction was allowed to proceed as in the Example 1 above. Similar experiments were then performed using known components and conditions for esterifications to make methyl formate (methanol and formic acid heated to about 65° C.), methyl propionate (methanol and propionic acid heated to about 67° C.), ethyl butyrate (ethanol and butyric acid heated to about 85° C.), ethyl propionate (ethanol and propionic acid heated to about 83° C.), ethyl n-butyrate (ethanol and n-butyric acid heated to about 85° C.), and ethyl iso-butyrate (ethanol and iso-butyric acid heated to about 85° C.). Conversion efficiencies were determined in each run and were found to compare very favorably with the yield data claimed for batch processes of making such esters using known acid catalysts. Rate of production calculations were also made consistent with Examples 3-7 above for the 1.0 μm air bubbler diameter used. These rate calculations also compared favorably to control tests run for each esterification reaction. Overall, these additional experiments using applicants' preferred method and apparatus constituted significant improvements over known processes, producing their respective esters at levels of purity exceeding 99.5% and yielding significant quantities of ester which were "naturally-made" without the use of conventional acid catalysts such as previously described. Representative examples of these calculations are shown in Table 2 which follows:

TABLE 2

| Products | Rate of Production (m/L/h) | Conversion Efficiency |
| --- | --- | --- |
| Ethyl Acetate | 0.0473 | 87.4% |
| Ethyl Propionate | 0.0563 | 84.6% |
| Ethyl n-butyrate | 0.0393 | 81.3% |
| Ethyl i-butyrate | 0.0287 | 82.7% |

Referring now generally to advantages encountered with applicants' preferred process and apparatus as exemplified in the above Examples, it is to be appreciated that these resultant esters are highly pure products in significant contrast to known methods of producing such "naturally-made" esters. For example, the ethyl acetate produced in applicants' Example 1 above had a purity in excess of 99.5%, whereas known processes seldom obtain purity levels in excess of 92%. In addition, the few impurities which do remain contain no sulfites or other contaminants which are unacceptable in food or pharmaceutical products. It is also to be appreciated that applicants' preferred process is environmentally friendly. In addition to the desired ester, the only products are water and weak solutions of the reactants themselves which can be reused in future esterifications. No harmful by-products are created which may be released to the environment. Also, applicants' esters are obtained at significantly lower costs than other "naturally-made" esters. For example, at current market prices the cost of "naturally-made" ethyl acetate has been approximately $10.00/lb. With applicants' method above, the cost is dropped to approximately $2.00/lb in experiments to date and is anticipated to be even lower in commercial applications.

Although applicants' preferred process has been described in part through specific examples of only a relatively few low-boiling esters, it is to be appreciated that the disclosed embodiment also has application with other low-boiling esters such as methyl acetate, methyl butyrate, n-propyl acetate, tert-butyl acetate and the like when their respective aliphatic monohydric alcohols and lower monocarboxylic acids are used. For the purposes of this disclosure, a "low-boiling ester" is intended to mean a monoester with a boiling point of less than about 125° C., an "aliphatic monohydric alcohol" is intended to mean a hydroxyl-containing hydrocarbon having from one to about four carbon atoms and a single hydroxyl group, and a "lower monocarboxylic acid" is intended to mean a carboxylic acid having between one and about four carbon atoms in the chain. The specific alcohol/carboxylic acid combinations used to make a particular ester are known or readily available to those skilled in the art, and the precise reactants and conditions selected as well as possible modifications in the preferred apparatus employed with applicant's invention are well within the knowledge and experience of such persons without requiring undue experimentation.

It is to be appreciated that the processes described herein utilize and produce reactants which may be flammable and/or otherwise hazardous under certain reaction conditions. It is understood that those skilled in the art can adapt the methods of the present invention to a particular application while maintaining appropriate environmental and occupational safety standards.

It is also to be appreciated that the process described herein is particularly adaptable to commercial applications. As has been noted, the selection of various reaction parameters may be accomplished by those skilled in the art without undue experimentation. Accordingly, various commercial embodiments are contemplated, and are considered to be within the scope of the present invention.

It is still further to be appreciated that applicants' reaction is most effective when a substantial amount of the ethyl acetate or other ester is removed from the reaction vessel during the reaction process. This removal is, of course, aided by the heating and air bubbling techniques disclosed herein. The continual removal of ester also helps to keep the reaction from reaching equilibrium, thereby driving the reaction with increased efficiency.

Finally, these and other variations are contemplated to be within the scope of applicants' invention and may be included to adapt the process and apparatus of the above embodiments to the manufacture of a particular ester desired. Therefore, while the invention has been described in detail in the foregoing disclosure and examples, the same are to be considered illustrative and not restrictive in character. It is to be understood that only the preferred embodiments have been shown and described, and that all changes and modifications within the spirit of the invention are desired to be protected.

We claim:

1. In a method for preparing an ester by mixing an alcohol with a carboxylic acid to form a reaction mixture, wherein the mixture reacts to form an esterification product, the improvement comprising removing the esterification product from the reaction mixture by bubbling a gas inert to the esterification reaction through the mixture during the reaction while the mixture is at a temperature of at least about the boiling point of the alcohol.

2. A method according to claim 1 wherein the mixture is further at a temperature below about the boiling point of the carboxylic acid.

3. A method according to claim 1 and further comprising condensing the vapors produced during said bubbling and recovering the esterification product therefrom.

4. A method according to claim 1 wherein the alcohol is an aliphatic monohydric alcohol having from one to about four carbon atoms and the carboxylic acid is a lower monocarboxylic acid having from one to about six carbon atoms.

5. A method according to claim 4 wherein the alcohol is selected from a group consisting of methanol, ethanol, n-propanol, iso-propanol and n-butanol, and the carboxylic acid is selected from a group consisting of formic acid, acetic acid, propanoic acid, n-butyric acid and iso-butyric acid.

6. A method according to claim 4 wherein the alcohol is ethyl alcohol and the carboxylic acid is acetic acid.

7. A method according to claim 1 and further comprising increasing the efficiency of said removing by decreasing the size of gas bubbles passing through the mixture during the reaction.

8. A method according to claim 7 wherein said bubbling is of gas bubbles that are less than about 1000 $\mu$m in diameter.

9. A method according to claim 8 wherein said bubbling is of gas bubbles that are less than about 10 $\mu$m in diameter.

10. A method according to claim 9 wherein said bubbling is of air.

11. In a method according to claim 1 wherein the reaction occurs without the use of an acid catalyst.

12. A method according to claim 1 and further comprising heating the reaction mixture to said temperature and maintaining said temperature during said bubbling.

13. A method according to claim 12 wherein said heating and said maintaining is to a temperature between about the boiling point of the alcohol and about 15° C. thereabove.

14. A method according to claim 13 wherein said heating and said maintaining is to a temperature between about the boiling point of the alcohol and about 5° C. thereabove.

15. A method according to claim 12 wherein said heating and said maintaining is to a temperature below about the boiling point of the carboxylic acid.

16. A method according to claim 15 and further comprising condensing the vapors produced during said bubbling and recovering the esterification product therefrom.

17. A method according to claim 16 wherein said removing and said recovering are at a conversion efficiency of about at least 85% in terms of carboxylic acid consumed during the reaction.

18. A method according to claim 17 wherein said removing and said recovering are of the esterification product at a purity level of about 99.5%.

19. A method according to claim 18 wherein the alcohol is ethyl alcohol and the carboxylic acid is acetic acid.

20. A method according to claim 19 wherein said removing is effective to remove a substantial amount of the ethyl acetate from the reaction mixture immediately after it is formed.

21. A method according to claim 20 wherein the reaction occurs without the use of an acid catalyst.

22. An apparatus for preparing esters, comprising:
a reaction vessel equipped with a fractionating column for mixing and reacting an alcohol and a carboxylic acid to form an esterification product;
means for bubbling a gas inert to the esterification reaction through the reaction mixture in said vessel to remove the esterification product from the mixture during the reaction, wherein said gas bubbles can exit said vessel only through the fractionating column;
means for heating and maintaining the mixture in said vessel at a temperature of at least about the boiling point of the alcohol during the reaction; and
means including the column for condensing and collecting vapors produced during the reaction and for recovering the esterification product therefrom.

* * * * *